United States Patent [19]

Prevorsek et al.

[11] 4,056,973
[45] Nov. 8, 1977

[54] TESTING VISCOELASTIC SOLIDS

[75] Inventors: Dusan C. Prevorsek; Young D. Kwon; Raj K. Sharma, all of Morristown, N.J.

[73] Assignee: Allied Chemical Corporation, Morris Township, N.J.

[21] Appl. No.: 750,039

[22] Filed: Dec. 13, 1976

[51] Int. Cl.² ............................................. G01N 3/34
[52] U.S. Cl. ......................................... 73/91; 73/15.6
[58] Field of Search ..................... 73/95, 91, 100, 15.6

[56] References Cited

U.S. PATENT DOCUMENTS

| | | | |
|---|---|---|---|
| 1,558,594 | 10/1925 | Coffin | 73/95 X |
| 2,916,912 | 12/1959 | Gibson | 73/91 |
| 3,214,969 | 11/1965 | Swanson | 73/91 |
| 3,826,902 | 7/1974 | Claxton et al. | 73/95 X |

Primary Examiner—Jerry W. Myracle
Attorney, Agent, or Firm—Gerhard H. Fuchs; Ernest A. Polin

[57] ABSTRACT

An apparatus and method for testing viscoelastic solids, such as tire cord. The apparatus includes: holding means, pretension means, first and second displacement generators, and mechanical-electrical transforming means. The holding means holds the material in a predetermined position. The pretension means applies tension during testing. The first displacement generator has an eccentric means for applying cyclic displacement. The second displacement generator applies cyclic displacement to the material co-directional with that applied by the first displacement generator, but of smaller amplitude and higher frequency. The mechanical-electrical transforming means transforms mechanical motion into electrical signals, such as a stress signal, a strain signal and a differentiated strain signal. The apparatus may also include means for differential testing of duplicate material samples wherein one sample is subjected to cyclic displacement of both the first and second displacement generators, and the other sample is subjected to cyclic displacement of the first displacement generator only. The apparatus may further include integrating means for integration of a stress-strain hysteresis loop. The method includes: applying a basic substantially sinusoidal strain wave having superimposed a cyclic strain wave of smaller amplitude and higher frequency than the basic strain wave to the material, with resulting stress developed in the material; transforming the resultant strain into an electrical strain signal having a strain wave form; transforming the resulting stress into an electrical composite stress signal having a composite stress wave form; and determining cyclic changes in that component of the composite stress signal resulting from the superimposed strain wave as a function of the basic strain wave.

30 Claims, 12 Drawing Figures

TESTING VISCOELASTIC SOLIDS

BACKGROUND OF THE INVENTION

This invention relates to determination of stress-related reversible changes in viscoelastic materials by cyclic deformation of structures such as plastic materials, especially fibrous materials such as tire cord.

Commonly assigned U.S. Pat. No. 3,969,930 issued July 20, 1976 to D. C. Prevorsek et al. discloses an apparatus and method for testing and measuring viscoelastic solids by applying strain to the material in a substantially sinuosoidal strain wave form with resulting stress within the material as it is subjected to such strain, transforming the strain applied into an electrical strain signal having a substantially sinusoidal strain wave form, transforming the resulting stress into an electrical stress signal, having a stress wave form which may be sinusoidal or nonsinusoidal. Observations of the phase lag between the strain wave form and the stress wave form, which phase lag varies in amount and sometimes in direction depending on the characteristics of the material, permits certain conclusions to be drawn about the performance of the material in use.

We have now found that changes in viscoelastic properties as function of the stress history and the reversible changes during cyclic loading correlate with certain technologically important properties, such as creep, time to break, tendency to stress craze, etc. Hence, it is desirable to provide a method and apparatus for determining stress-related changes in viscoelastic properties, such as involving elastic modulus and mechanical loss as a function of strain.

When an elastic material is subjected to cyclic deformation under prestrain, the strain $\gamma$ varies according to $$\gamma(\theta) = \gamma_0 + \Delta\gamma \sin\theta$$

wherein $\gamma_0$ is the prestrain, $\Delta\gamma$ represents the strain amplitude and $\theta$ is the angle.

With linear viscoelastic solids the resulting stress wave is sinusoidal and shifted on the angle scale by the phase angle difference $\delta$, so that the stress $\Theta$ is represented by $$\sigma(\theta) = \sigma_0 + \Delta\sigma \sin(\theta + \delta)$$

In this case, $\delta$ and $\Delta\sigma$ are constant. The fraction $\Delta\sigma/\Delta\gamma$ represents the complex modulus $E_*$.

When the stress wave resulting from a sinusoidal strain wave is not sinusoidal, the distortion of the stress wave can result from changes in modulus as function of strain (or angle $\theta$) along the cycle, or changes in mechanical loss as function of strain (or angle $\theta$) during the cycle, or a combination of both, as expressed by the following equation:

$$\sigma(\theta) = \sigma_0 + \Delta\sigma(\theta)\sin[\theta + \delta(\theta)]$$

The present invention provides a method and apparatus to determine $\Delta\sigma(\theta)$ and $\delta(\theta)$.

The determination of $\Delta\sigma(\theta)$ and $\delta(\theta)$ requires determination of material modulus and loss at each instant of the experiment. In accordance with the present invention this is achieved by subjecting the material to a basic, substantially sinusoidal strain wave having superimposed a cyclic strain wave of smaller amplitude and higher frequency than the basic strain wave, and extracting the desired information from the resultant composite stress wave. Thus, it is possible to carry out viscoelastic measurements which in turn reflect the material structure, while the sample is subjected to various loading histories.

SUMMARY OF THE INVENTION

The apparatus and method of the present invention is adapted for testing a viscoelastic material. The apparatus includes: holding means, pretension means, first and second displacement generators, and mechanical-electrical transforming means. The holding means is connected to the material for holding the material in a predetermined position during testing. The pretension means is coupled to the material for applying tension to the material during testing. The first displacement generator has an eccentric means coupled to the material for applying cyclic displacement to the material, of predetermined amplitude and frequency. The second displacement generator is coupled to the material for applying cyclic displacement to the material of predetermined frequency and amplitude co-directional with the cyclic displacement applied by the first displacement generator. Desirably, the amplitude and frequency of the cyclic displacement applied to the material by the second displacement generator are predetermined such that the ratio of the amplitude of the cyclic displacement applied by the second displacement generator to the amplitude applied by the first displacement generator is within the range of from about 1:5 to about 1:100, and the frequency of the cyclic displacement applied by the second displacement generator is from about 20 to about 200 times the frequency applied by the first displacement generator.

The apparatus may also include means for differential testing of duplicate samples of the same material wherein the first sample is subjected to cyclic displacement of both the first and second displacement generator, and the second sample is subjected to cyclic displacement of the first displacement generator only. The differential observed between the stress waves of the first and second samples is the stress wave generated by the second displacement generator.

The mechanical-electrical transforming means is coupled to the material for transforming mechanical motion into electrical signals.

The mechanical-electrical transforming means includes: a first force transforming means, a second force transforming means, and, optionally, third, fourth, fifth and sixth force transforming means. The first force transforming means transforms mechanical stress developed in the material by the combined strain applied by both the first and second displacement generators into an electrical composite stress signal. The second force transforming means transforms mechanical strain applied to the material by the first displacement generator into an electrical strain signal. The optional third force transforming means is employed in differential testing of duplicate samples of the same material, as above described, and transforms mechanical stress developed in one of the duplicate samples of the material by the stress applied by the first displacement generator only. The optional fourth force transforming means transforms mechanical strain applied to the material by the second displacement generator into an electrical strain signal. The optional fifth and sixth force transforming means are arranged at an angle of 90° with reference to the fourth and second force transforming means, respectively. The fifth and sixth force transforming means are mechanical differentiating means which transform a time derivative of mechanical strain applied to the material into an electrical cosine signal. The fifth force transforming means transforms a time derivative of mechanical strain applied to the material by the second displacement generator; the sixth force transforming means transforms a time derivative of mechanical strain applied to the material by action of the first displacement generator.

The apparatus including means for differential testing of duplicate samples of the same material, as above described, may also include: means for successively isolating discrete strain and corresponding stress signals representing successive single displacement cycles resulting from action of the second displacement generator; means for integrating a stress/strain hysteresis loop for successive displacement cycles; and display means for displaying an output of the integrating means to measure the areas of the successively integrated hysteresis loops and to thereby determine energy loss as a function of the cyclic displacement resulting from the action of the first displacement generator.

The strain signal generated by the first displacement generator has at least a substantially sinusoidal wave form. The strain signal generated by the second displacement generator, which is superimposed on the strain signal generated by the first displacement generator, desirably, but not necessarily, has also substantially sinusoidal wave form.

The resultant stress signals may each have nonsinusoidal or sinusoidal wave form. There is a phase lag between the stress signals and the strain signals resulting from the strain waves generated by the first and second displacement generators each, and the phase lag may vary in amount and direction as a function of time. Where the phase lag varies in amount and direction the stress signal lags in time behind the strain signal during expansion of the material and the strain signal lags in time behind the stress signal during contraction of the material. The phase lag between the stress signal and the strain signal resulting from the strain wave generated by the second displacement generator may vary in amount and direction not only as a function of time, but additionally as a function of the strain applied by the first displacement generator. There may also be change in amplitude of the stress signal resulting from the strain applied by the second displacement generator, which change in amplitude is a function of the strain applied by the first displacement generator.

The method includes the following steps: applying a first cyclic sinusoidal strain component to the material to be tested, having predetermined amplitude and frequency; applying a superimposed second sinusoidal strain component to the material to be tested, having predetermined amplitude and frequency; transforming the strain applied by the first cyclic strain component into an electrical strain signal having a cyclic strain wave form and an amplitude; and transforming the stress resulting in the material from the strain applied by the first and second cyclic strain components into a composite electrical stress signal. The method further includes observing that there is a change in amplitude of that component of the composite stress signal resulting from the strain applied by the second cyclic strain component, which varies with the strain applied by the first cyclic strain component.

The method may also involve differential testing including the following steps: applying a first cyclic sinusoidal strain component of predetermined amplitude and frequency to a first and second sample of the material to be tested; applying a superimposed second cyclic sinusoidal strain component of predetermined amplitude and frequency to the second sample of the material to be tested; transforming the strain applied by the first strain component into an electrical strain signal having a cyclic strain wave form and an amplitude; transforming the strain applied by the second strain component into an electrical strain signal having a cyclic strain wave form and an amplitude; transforming the stress resulting in the first sample of the material when the strain of the first strain component is applied to that sample into a stress signal; transforming the composite stress resulting in the second sample of the material when the strain of both the first and second strain components is applied to that sample into a composite stress signal; obtaining a stress resulting from the strain applied by the second strain component on the second sample as the difference between the stress signals obtained for the first and second samples. The differential method of testing may include observing that there is a change in amplitude of the stress signal resulting from the strain applied by the second strain component on the second sample, which change in amplitude varies with the strain applied by the first strain component.

The differential method of testing may further include observing that there is a phase lag between the strain wave form applied by the second strain component and the stress wave form resulting therefrom, and that the phase lag varies in amount and sometimes in direction, depending upon (a) the characteristics of the material being tested and (b) the strain applied by the first strain component.

The step of observing that the phase lag varies in amount and sometimes in direction as a function of the strain applied by the first strain component includes: separately displaying discrete successive stress waves of the second strain component, which may be consecutive or non-consecutive, along a vertical axis; displaying the corresponding discrete strain wave along a horizontal axis; observing the formation of the hysteresis loop for each separate display. The areas within the separately formed hysteresis loops reflect the energy loss in the second sample of the material as a function of the strain applied by the first strain component. The step of measuring the area within each separately formed hysteresis loop may include using an integrating means to measure such area. A step of using an integrating means may optionally include: transforming the strain applied to the second sample of the material by the second strain component into a differentiated strain signal; and integrating the differentiated strain signal and the corresponding stress signal. The step of transforming the strain applied to the second sample of the material by the second strain component into a differentiated strain signal includes: differentiating the strain mechanically by an arrangement of a differentiating mounting means at an angle of 90° with reference to a strain mounting means.

DESCRIPTION OF THE DRAWINGS

FIG. 2 shows the pretension means.

FIG. 3 shows an eccentric mechanical means and an embodiment of a stress mounting means.

FIG. 4 shows an embodiment of the second displacement generator with associated optional mechanical-electrical force transforming means.

DETAILED DESCRIPTION

General Orientation

Figure 1:
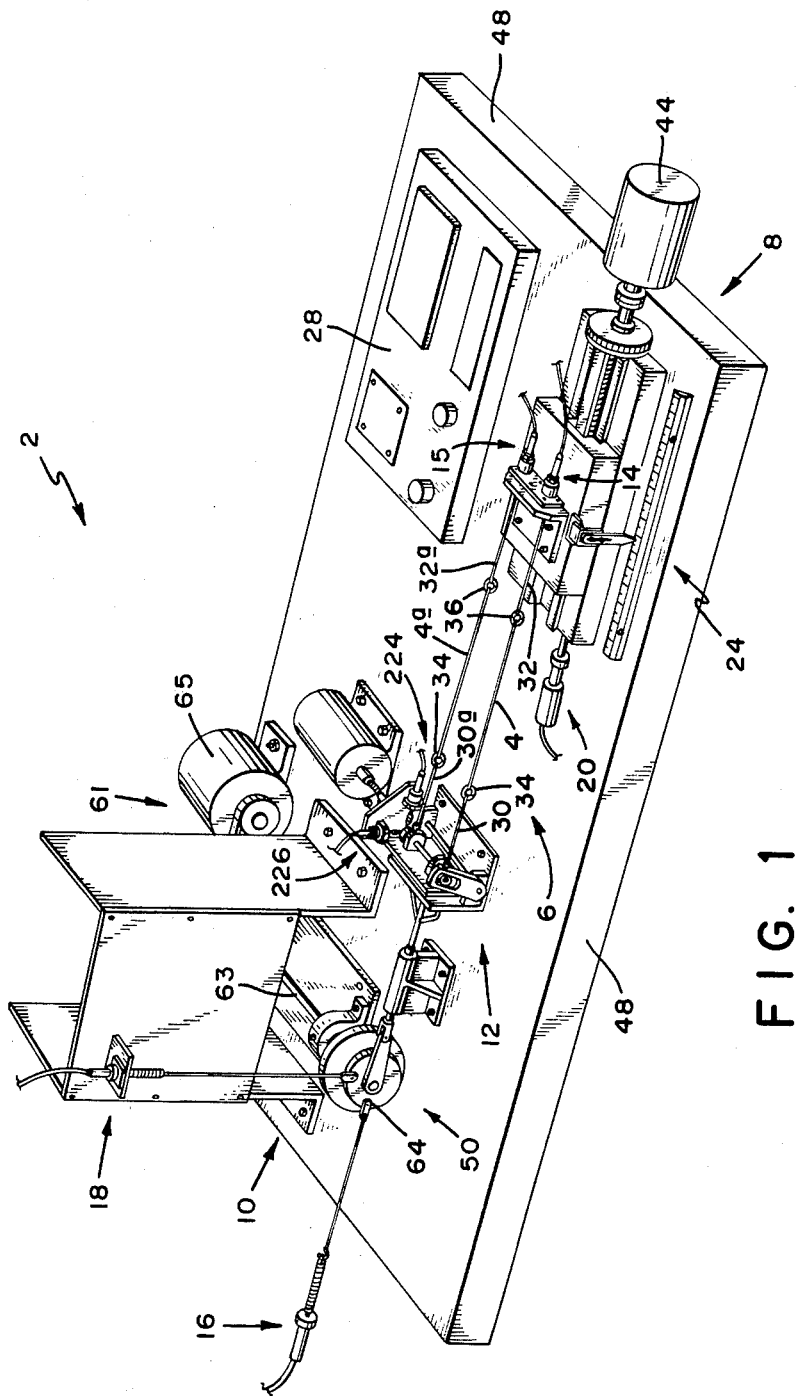
FIG. 1 is an isometric view of major portions of the apparatus of the present invention, including optional differential testing means and optional mechanical-electrical transforming means associated with the second displacement generator.

Referring to FIG. 1, the apparatus of the present invention, referred to generally by the numeral 2, is adapted for non-differential as well as differential testing of a viscoelastic solid material. A viscoelastic material is a material possessing viscous properties and elastic properties. For example, the material may be a strand of monofilament or multifilament material. The multifilament or polyfilament material may, for example, be a specimen of tire cord made of polymeric fiber and used for reinforcing pneumatic tires. The material to be tested may also be a yarn, film, rod or solid block of material. In the primary embodiment, illustrated in FIGS. 1-5, the material 4 and, optionally, 4a is a multifilament tire cord which may be tested under conditions which simulate conditions existing when a tire containing such tire cord is running on a vehicle, such as an automobile or truck. The material is tested to determine and measure selected physical-structural properties of the material, including its ability in the presence of heat to withstand stress, strain and physical-structural fatigue. The apparatus 2 is specially adapted to determine cyclic changes in modulus E and loss as a function of strain.

The apparatus 2 includes the following major components: a holding means 6; a pretension means 8; a first sinusoidal displacement generator 10; a second sinusoidal displacement generator 12 and mechanical-electrical transforming means. The mechanical-electrical transforming means are indirectly coupled to the material 4 and, optionally, 4a, and are adapted for transforming mechanical motion in the material into electrical signals. The mechanical-electrical transforming means includes: first force transforming means 14 for generation of a composite stress signal; optional second force transforming means 16 for generation of a basic strain signal; optional third force transforming means 15 for generation of a basic stress signal for differential testing; optional fourth force transforming means 224 for generation of a superimposed strain signal; optional fifth force transforming means 226 for generation of a differentiated superimposed strain signal; and optional sixth force transforming means 18 for generation of a differentiated basic strain signal. Fifth and sixth force transforming means 224 and 226, respectively, are both associated with second displacement generator 12. The mechanical-electrical transforming means may further include a position transforming means 20. Preferably, the apparatus 2 also includes: a permanent elongation means 24; and an integrating means 28.

Prior to testing, the viscoelastic material 4 and, optionally, 4a, is formed into a shape suitable for mounting in the holding means 6. For example, the material may be formed into a closed loop. The closed loop may be achieved by using a length of material which preferably is in the range between 4 and 16 inches. The material has two loose ends which are tied together by a knot. The closed loop has a length which is approximately one-half of the length of material before the knot is tied. Preferably, the closed loop has a length in the range between 2 and 8 inches. The holding means 6 is connected to the closed loop of material 4 and, optionally, 4a, and is adapted for holding the material in a predetermined position during testing, preferably in a horizontal plane.

Holding Means

Referring to FIG. 1, for purposes of testing for stress and strain the holding means 6 includes two (for optional differential testing two pairs) substantially rigid structural members, preferably lengths of stiff wire, an active wire 30 (and, optionally, 30a) and a passive wire 32 (and, optionally, 32a). One end of the active wire, the end adjacent to the material, has an engaging means, such as a hook 34, for engaging the material. Likewise, one end of the passive wire, the end adjacent to the material, also has an engaging means, such as a hook 36, for engaging and holding the material. The other end of the active wire 30 is actively connected to second displacement generator 12, to be subjected to concurrent displacement by both first displacement generator 10 and second displacement generator 12. The other end of optional active wire 30a is actively connected to first displacement generator 10. The other end of the passive wire 32 (and, optionally, passive wire 32a) is connected to the pretension means 8. The knot in the loop of the viscoelastic material is preferably arranged either at the hook 34 of the active wire or at the hook 36 of passive wire to avoid or at least minimize loosening, untying or elongation in the knot during testing and to avoid testing variation between the length of the loop which does have the knot and the length of the loop which does not have the knot. The active wire and the passive wire should have negligible weight, and they should also have a negligible amount of twist, the latter in order to avoid variations in their length during testing. Preferably, the active and passive wires are constructed of a rigid, monofilament metal wire, such as piano wire.

Pretension Means

Figure 2:
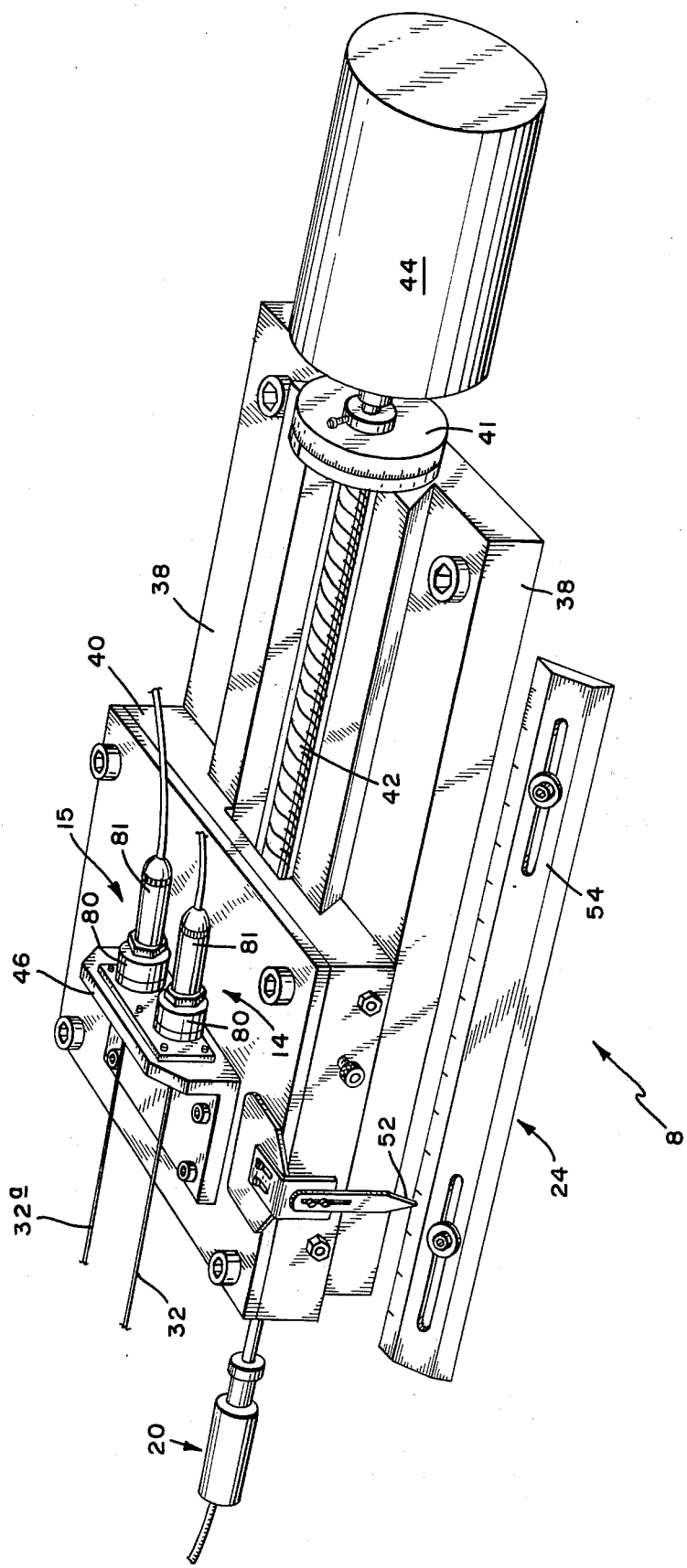
FIG. 2 is an isometric view of a portion of FIG. 1.

Referring to FIG. 2, the pretension means 8 is adapted for applying tension to the passive wire 32 and, optionally, passive wire 32a, and indirectly to the material during testing. The pretension means 8 includes: a stationary member 38; a movable member 40; a lead screw 42; and, optionally, a servo motor 44. Periodic manual adjustment may be substituted for the continuous automatic adjustment provided by the servo motor. The end of the passive wire 32 which is opposite from the material 4 is connected to the first force transforming means 14 which is mounted by means of an L-shaped bracket 46 on the movable member 40. For optional differential testing, third force transforming means 15 are provided, as shown, to which there is connected passive wire 32a. Referring to FIG. 1, the stationary member 38 is mounted on a platform 48. The movable member 40 is mounted on the stationary member 38. The lead screw 42 is arranged between the movable member 40 and the stationary member 38. One end of the lead screw 42 is connected to the movable member 40 and the other end of the lead screw 42 is connected to servo motor 44. The lead screw 42 has screw threads which engage screw threads on a channel in the top of the stationary member 38 and screw thread in a channel on the bottom of movable member 40. The pretension means 8 applies a selected amount of tension, preferably constant tension, to the material 4 and, optionally, 4a by means of the lead screw 42 and the servo motor 44. Gradually, the servo motor 44 rotates the lead screw 42 in a direction so as to draw the movable member 40 toward the servo motor 44. As a result, the movable member 40 moves with reference to the stationary member 38 toward the servo motor 44 during testing of the material. Such movement of the movable member 40 compensates for transitory or permanent elongation or contraction in the material during testing and provides a constant tension on the material.

The permanent elongation means 24 determines the permanent elongation occurring in the material during testing. Permanent elongation is sometimes referred to as "creep". The permanent elongation means 24 includes a pointer 52 and a scale 54 which provide an approximate measurement of changes in length of the material. The pointer 52 is mounted on the movable member 40 of the pretension means 8. The scale 54 is mounted on the platform 48 adjacent to the stationary member 38 of the pretension means 8. In operation, the pointer 52 indicates the lengths of the material before and after testing. The difference in lengths is the permanent elongation which occurred in the material during testing.

The pretension means 8 also includes a graduated dial 41 on an end of the lead screw 42 adjacent to the servo motor 44. The graduated dial 41 indicates the amount of rotation of the lead screw 42 and the amount of movement of the movable member 40 during testing. The position transforming means 20 may be an electronic cell, such as a linear voltage differential transformer. The position transforming means 20 and the graduated dial 41 provide more accurate measurement of changes in length of the material 4, than the permanent elongation means 24, especially as to transitory changes.

First Displacement Generator

Figure 3:
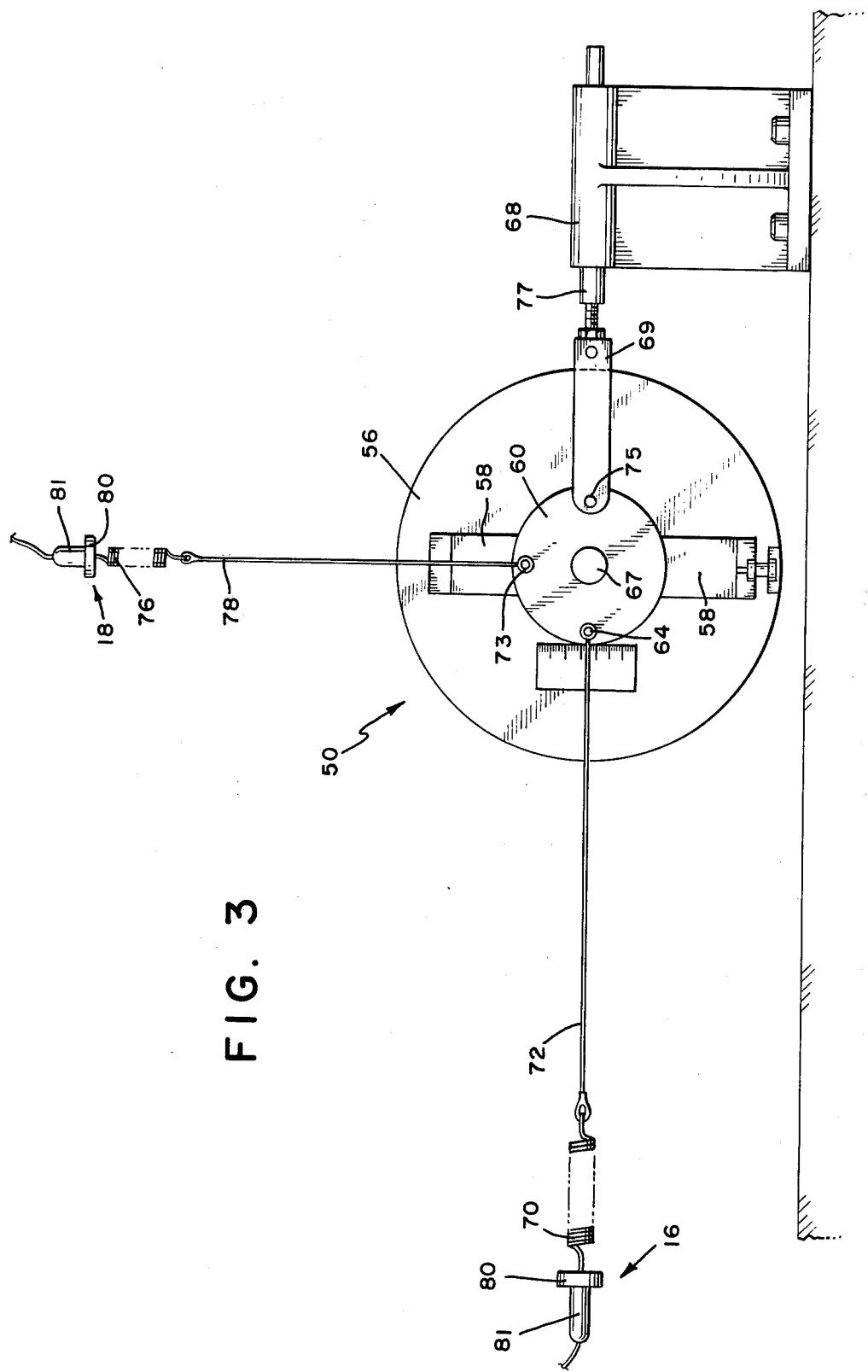
FIG. 3 is a frontal view of a portion of FIG. 1.

Referring to FIGS. 1 and 3, the first displacement generator 10 has an eccentric means 50 directly coupled to second displacement generator 12. The first displacement generator 10 is adapted for applying repetitive and cyclic, sinusoidal displacement as sinusoidal strain to the material. The first displacement generator 10 controls the strain applied to the material and allows the stress to vary. As a result, the viscoelastic material undergoes at least substantially sinusoidal strain and preferably strain which is as precisely sinusoidal as possible. The material also undergoes either nonsinusoidal or sinusoidal stress, as well as tension and physical-structural fatigue. The eccentric means 50 may preferably be mechanical, but may also be electromechanical. The eccentric means 50 of the displacement generator 10 includes: a concentric head 56; an eccentric slide 58; a centerpiece 60; and a drive means 61.

The drive means 61 provides a source of rotating power to the eccentric mechanical means 50. The drive means 61 includes a drive shaft 63, a drive motor 65, a speed reducer (not shown) and a speed control (not shown). The concentric head 56 is rotatable on the drive shaft 63 and is driven by the drive motor 65. The speed control allows control and variation of the speed of rotation of the drive motor 65, drive shaft 63 and concentric head 56 in order to simulate various speeds of rotation of a tire on a vehicle. The concentric head 56 has a center which is concentric with the drive shaft 63.

Referring to FIG. 3, the circular centerpiece 60 is mounted on the eccentric shaft 67 of the eccentric slide 58. The eccentric shaft 67 extends into a hole in the center of the centerpiece 60 and is rotatable with reference to the centerpiece 60. The eccentric shaft 67 transmits cyclic displacement to the material. The centerpiece 60 has a center which is concentric with the shaft 67 of the slide 58 and eccentrically displaced from the center of the concentric head 56.

The centerpiece 60 includes: a stress mounting means 75, a strain mounting means 64 and a differentiating mounting means 73, each of which are indirectly coupled to the material. One end of a stress arm 69 is rotatably mounted by the stress mounting means 75, such as a pivot point, on the outer periphery of the centerpiece 60. The opposite end of the stress arm 69 is indirectly coupled to second displacement generator 12 and the material by means of a stress rod 77 which slidably passes through a first linear bearing 68. The strain mounting means 64, such as a pivot point, is rotatably mounted on the outer periphery of the centerpiece 60. The strain mounting means 64 is connected to a strain wire 72, which in turn is connected to a strain spring 70, which in turn is connected to the second force transforming means 16. The differentiating mounting means 73, such as a pivot point, is also rotatably mounted on the outer periphery of the centerpiece 60. The differentiating mounting means 73 is connected to a differentiating wire 78 which in turn is connected to a differentiating spring 76, which in turn is connected to the sixth force transforming means 18. The strain mounting means 64 and the differentiating mounting means 73 are both indirectly coupled to the material by means of the stress arm 69, stress rod 77, second displacement generator 12 and the active wire 30 and, optionally, 30a.

The stress mounting means 75 is arranged at an angle of 90° with respect to the differentiating mounting means 73. The stress arm 69 is arranged colinearly with the strain wire 72, by arranging the stress mounting means 75 at an angle of approximately and preferably precisely 180° with respect to the strain mounting means 64. The differentiating mounting means 73 is arranged at an angle of 90° with respect to the stress mounting means 75 and with respect to the strain mounting means 64. It is desirable that the first force transforming means 14, an extended centerpoint of the eccentric head 56 and the drive shaft 63, and the second force transforming means 16 be colinear. Likewise, it is important that the sixth force transforming means 18 be perpendicular to the horizontal plane formed by the first force transforming means 14, the extended centerline of the concentric head 56 and the second force transforming means 16. This colinear arrangement provides advantages of design simplification and minimization of deflection error between the first force transforming means 14 and the second force transforming means 16.

Second Displacement Generator

Figure 4:
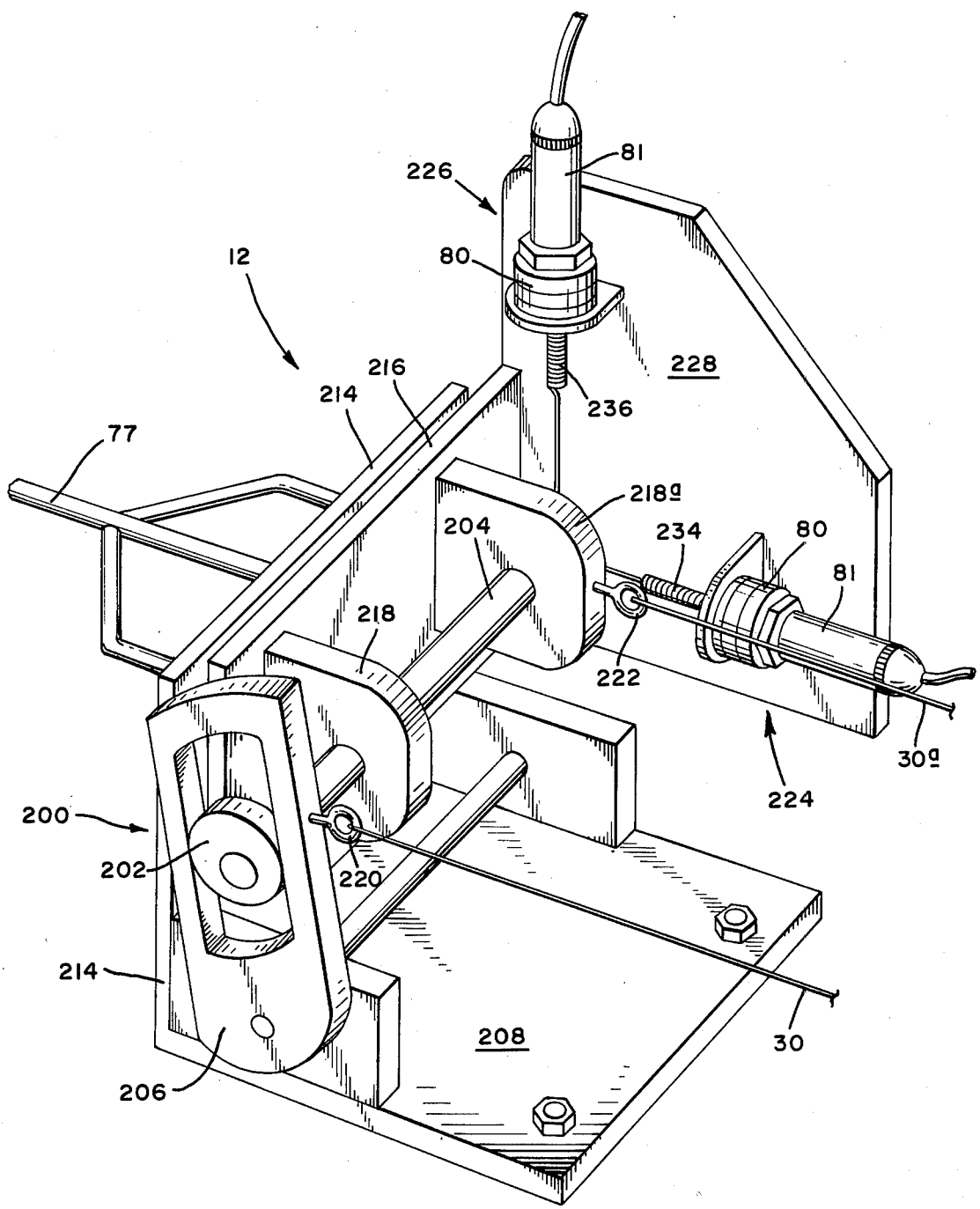
FIG. 4 is an isometric view of a portion of FIG. 1.
Figure 5:
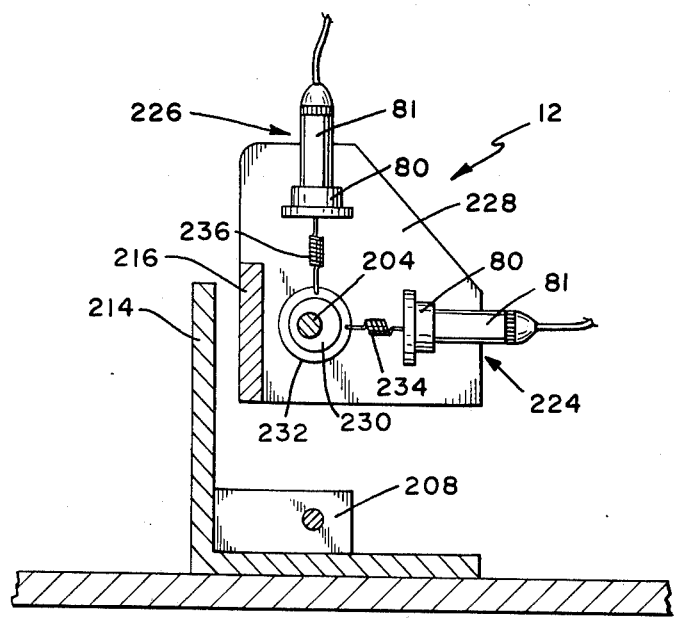
FIG. 5 is a cross-sectional view of the second displacement generator illustrated in FIG. 4 illustrating operation of optional mechanical-electrical force transforming means in cooperation therewith.

Referring to FIGS. 1, 4 and 5 the second displacement generator 12 has an eccentric means 200 indirectly coupled to the material to be tested through active wire 30. The second displacement generator is adapted for applying repetitive and cyclic, sinusoidal displacement as sinusoidal strain to the material, superimposed upon and co-directional with the repetitive and cyclic, sinusoidal displacement applied to the material by the first displacement generator 10. Like the first displacement generator 10, the second displacement 12 controls strain applied to the material and allows the stress to vary. As a result, the viscoelastic material is subjected to strain applied by a first substantially sinusoidal strain wave generated by the first displacement generator, having superimposed thereon a second substantially sinusoidal strain wave generated by the second displacement generator. The material also undergoes either nonsinusoidal or sinusoidal stress, as well as tension and physical-structural fatigue. The eccentric means 200 may preferably be mechanical, but it may also be electromechanical or hydraulic. The eccentric means 200 of second displacement generator 12 includes an eccentric head 202 fixedly mounted on rotatable shaft 204 and a slotted yoke 206 pivotably mounted on base 208 in engagement with eccentric head 202. Rotatable shaft 204 is coupled to a drive motor 210 by means of flexible coupling 212. Drive motor 210 is provided with a speed reducer (not shown) and a speed control (not shown). The speed control allows control and variation of the speed of rotation of rotatable shaft 204 and eccentric head 202, hence controls the frequency of the cyclic displacement applied to the material by the second displacement generator 12.

Base 208 has a raised front portion 214 which serves as a linear bearing for stress rod 77, which is further slidably supported by first linear bearing 68, then trifurcated into three tines each of which is passed through and slidably supported by raised front portion 214 of base 208. To the ends of the tines of stress rod 77 distal from first displacement generator 10 is affixed movable member 216, on which there are mounted bearings 218 and 218a supporting rotatable shaft 204. Stress rod 77 transmits the cyclic, sinusoidal displacement applied by first displacement generator 10 to movable member 216, and through bearings 218 and 218a, rotatable shaft 204 and eccentric head 202, to yoke 206. Yoke 206 is equipped with first hook 220 for holding active wire 30, to which the material to be subjected to cyclic displacement by both the first and second displacement generators is affixed. In operation, the first displacement generator subjects movable member 216, and components supported by it, including yoke 206 and hook 220, to a first cyclic sinusoidal strain component. Second displacement generator 12 applies a superimposed second cyclic sinusoidal strain component on yoke 206 and hook 220. The resultant composite strain is transmitted to the material to be tested by means of active wire 30.

For optional differential testing, as above described, a second hook 222 is affixed to movable member 218, directly or indirectly, for example to bearing 218a as illustrated in the drawings, which in turn applies cyclic, sinusoidal displacement generated by the first displacement generator 12 only via active wire 30a to a second sample of the material to be tested.

Force Transforming Means

Referring to FIGs. 1 and 2, the first and optional third force transforming means 14 and 15, respectively, each include a load cell 80 and an electronic cell 81, such as a mechanical-electrical transducer. The first and optional third force transforming means 14 and 15, respectively, are mounted on the bracket 46 of the pretension means 8. The first force transforming means 14 is indirectly coupled to the first sample of material 4 through the passive wire 32 and transforms mechanical stress developed into the first sample of material 4 by the combined action of the first and second displacement generators into an electrical stress signal (composite stress signal). The optional third force transforming means 15 is indirectly coupled to the second sample of material 4a employed in differential testing through passive wire 32a and transforms mechanical stress developed in the second sample of material 4a by the sole action of the first displacement generator into an electrical stress signal (basic stress signal).

Referring to FIGS. 1 and 3, the second force transforming means 16 includes a load cell 80 and an electronic cell 81, such as a mechanical-electrical transducer. The second force transforming means 16 is indirectly coupled to first displacement generator 10 by means of the strain spring 70, the strain wire 72 and strain mounting means 64. The second force transforming means 16 is also indirectly coupled to the first sample of material 4 (and, optionally, to the second sample of material 4a) through second displacement generator 12 and the active wire 30 (and optional second wire 30a, as the case may be) in order to transform mechanical strain applied to the material by the first displacement generator 10 into an electrical strain signal (basic strain signal). The active wire 30, and optional active wire 30a, reflect strain. The passive wire 32, and optional passive wire 32a, reflect stress.

Referring to FIGs. 1, 4 and 5, the optional fourth and optional fifth force transforming means 224 and 226, respectively, each include a load cell 80 and an electronic cell 81. The fourth and fifth force transforming means are both mounted on bracket 228 formed as part of movable member 216, and both are indirectly coupled to second displacement generator 12 as follows: rotatable shaft 204 of second displacement generator 12 is provided with a second eccentric head 230 providing eccentric movement in amplitude identical to that provided by eccentric head 202. Further, second eccentric head 230 is mounted in the same angular position as rotatable shaft 204 as is eccentric head 202, so that eccentric heads 202 and 230 provide identically phased displacement of identical amplitude. Second eccentric head 230 is in sliding engagement with follower 232. Fourth force transmitting means 224 is coupled to follower 232 by means of connecting spring 234. The fourth force transforming means generates an electrical strain signal corresponding to the strain applied to the material by the second displacement generator 12 (superimposed strain signal). The fifth force transforming means 226 is coupled to follower 232 by means of differentiating spring 236. The fifth force transforming means 226 generates an electrical differentiated strain signal which is a cosine wave signal corresponding to a mathematical differentiation of the strain signal from the fourth force transforming means 224 (differentiated superimposed strain signal). The mathematical differentiation is with respect to the angular position of the second eccentric head 230 around the rotatable shaft 204. Thus, the mechanical arrangement of the differentiating fifth force transforming means 226 mounted on bracket 228 at an angle of 90° with reference to the fourth force transforming means 224, both coupled to second displacement generator 12, constitutes a mechanical differentiating means which performs the function of differentiating the strain applied by the second displacement generator 12 mechanically, rather than electronically. Such mechanical differentiating means eliminates the noise that would be produced by an electronic differentiating means.

Referring to FIGS. 1 and 3, the optional sixth force transforming means 18 includes a load cell 80 and an electronic cell 81, such as a mechanical-electrical transducer. The sixth force transforming means 18 is indirectly coupled to the first displacement generator 10 by means of the differentiating spring 76 and the differentiating wire 78. The sixth force transforming means 18 generates an electrical differentiated strain signal which is a cosine wave signal corresponding to a mathematical differentiation of the strain signal from the second force transforming means 16 (differentiated basic strain signal). The mathematical differentiation is with respect to the angular position of the eccentric shaft 67 around the drive shaft 63. Thus, the mechanical arrangement of the differentiating mounting means 73 on the centerpiece 60 of the first displacement generator 10 at an angle of 90° with reference to the strain mounting means 64 in combination with the third force transforming means 18 constitutes a mechanical differentiation means which performs the function of differentiating the strain generated by the first displacement generator 10 mechanically, rather than electronically. Such mechanical differentation means eliminates the noise that would be produced by an electronic differentiation means.

Procesing of Electronic Signals and Display of Stress and Strain

Figure 6:
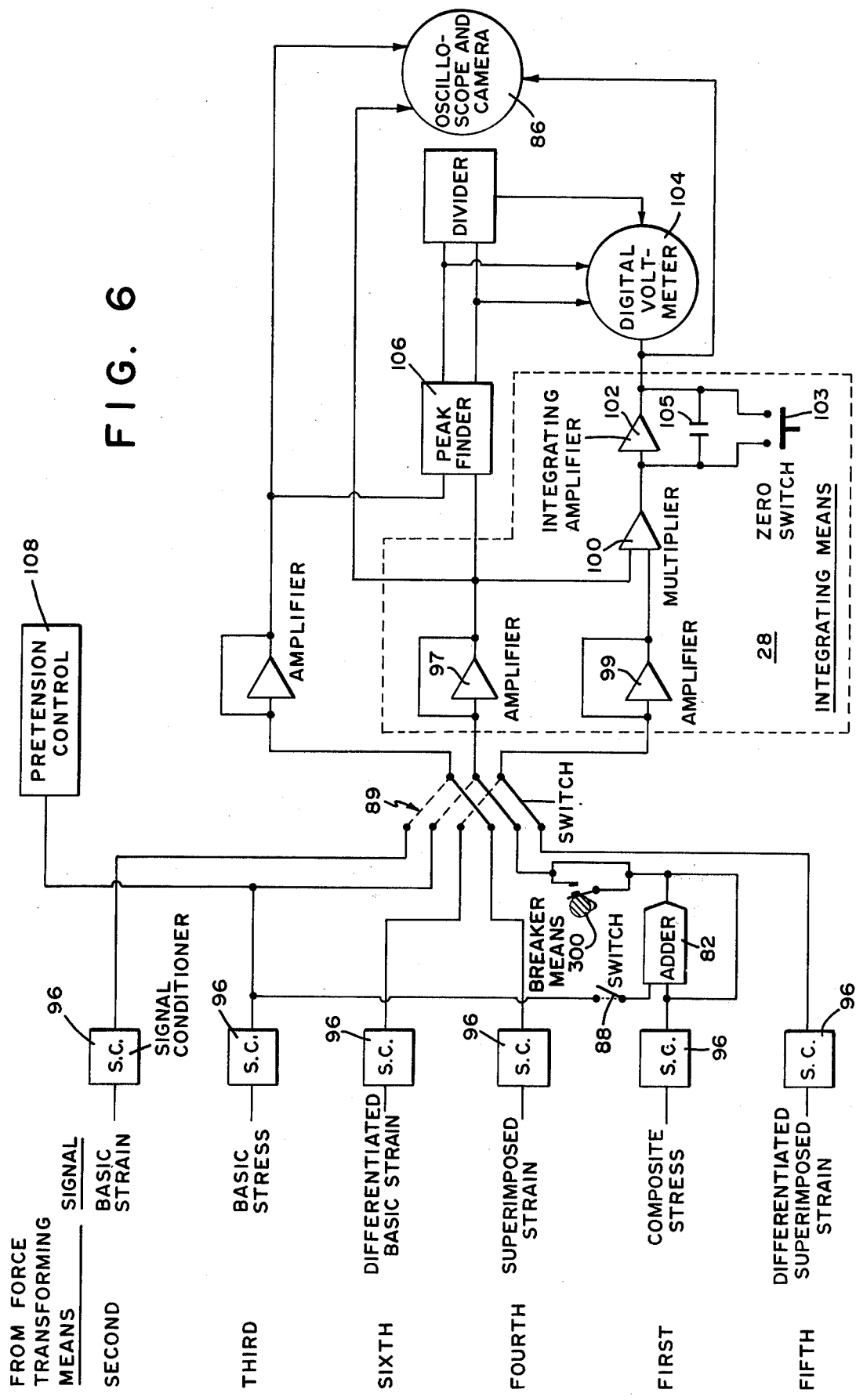
FIG. 6 is a schematic diagram of an electronic circuit for the apparatus shown in FIG. 1.

Referring to FIG. 6, the composite stress signal from the first force transforming means 14; the basic strain signal from the optional second force transforming means 16; the basic stress signal from the optional third force transforming means 15; the superimposed strain signal from the optional fourth force transforming means 224; the differentiated superimposed strain signal from the optional fifth force transforming means 226; and the differentiated basic strain signal from the optional sixth force transforming means 18 are processed in the following ways: These signals are each conducted first to a signal conditioner 96. Each signal conditioner includes an amplifier and a power supply. The power supply supplies power to the electronic cell 81 of each of the force transforming means for generation, respectively, of a composite stress signal, a basic strain signal, a basic stress signal, a superimposed strain signal, a differentiated superimposed strain signal, and a differentiated basic strain signal.

Figure 7:
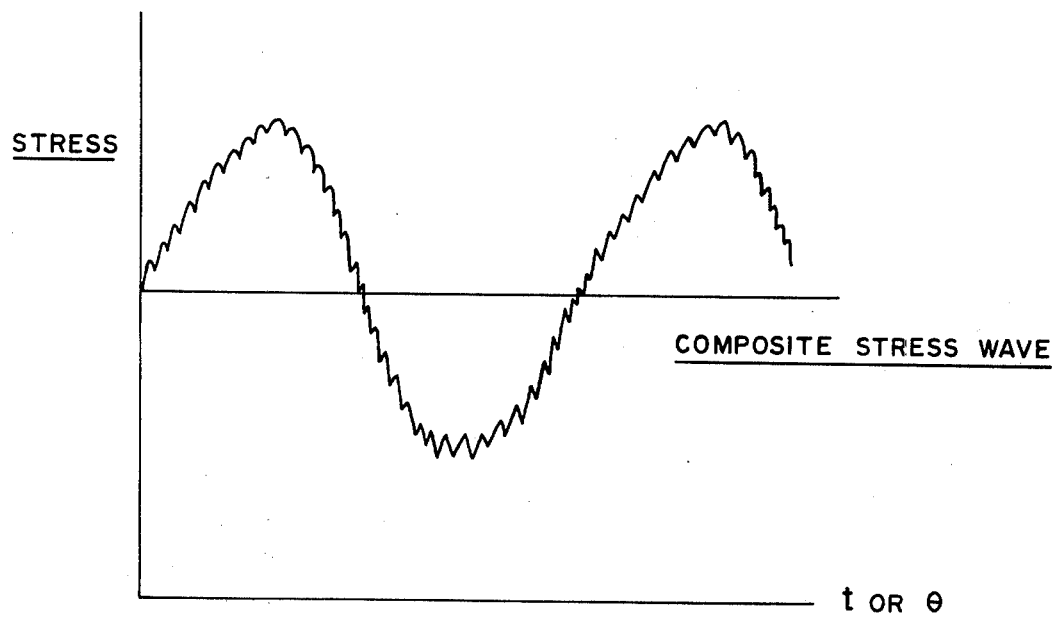
FIG. 7 is an illustration of a display of a strain signal obtained by non-differential testing.

With reference to FIG. 6, with switch 89 in the lower position as illustrated, the composite stress signal from signal conditioner 96 is conducted to a display means such as an oscilloscope 86, where it is displayed along a vertical axis which is proportional to voltage. Time ($t$), which is proportionate to angle $\theta$ of basic cyclic strain applied by first displacement generator 10, is displayed along the horizontal axis. An exemplary oscilloscope display of composite stress is shown in FIG. 7 of the drawings. From the oscilloscope display, or from a photographic record therof, one can determine if there is a cyclic change in amplitude of the superimposed stress wave and, if so, the extent of that change.

The superimposed strain signal and the superimposed stress signal, each as output of a signal conditioner 96, may also be individually displayed on a display means, such as the oscilloscope 86. Display of the superimposed stress unconfounded by the basic stress signal requires differential testing, as above described. Both, the superimposed strain signal as well as the superimposed stress signal, may be displayed along a vertical axis which is proportional to voltage. Time ($t$), which is proportionate to the angle of the superimposed cyclic strain, is displayed along the horizontal axis. Display of the superimposed strain signal generated by fifth force transforming means associated with second displacement generator 12 is analogous to that described above for the composite stress signal. To obtain the superimposed stress signal, unconfounded by the basic stress generated solely by application of the basic strain, one proceeds as follows: A basic stress signal is generated in sample of material 4($a$) by differential testing. With switch 88 in closed position, the basic stress signal as the output from a signal conditioner 96 is conducted to adder 82. The superimposed stress signal generated in sample of material 4 by differential testing, as the output from a signal conditioner 96, is also conducted to adder 82. The respective outputs are provided in opposite polarity, e.g. when the basic stress signal as obtained from the signal conditioner is provided as positive voltage, then the superimposed stress signal as obtained from the signal conditioner is provided as negative voltage. Conversely, when the basic stress signal is of negative voltage, then the superimposed stress signal is provided as positive voltage. The superimposed stress signal consists of two components: (1) the stress generated by the cyclic strain applied by the first displacement generator (basic stress signal), having superimposed thereon (2) the stress generated by the cyclic strain applied by the second displacement generator (superimposed stress signal). In adder 82, the basic stress signal obtained from sample of material 4($a$) in differential testing cancels out the basic stress signal component of the composite stress signal obtained from sample of material 4, so that the output of adder 82 represents the superimposed stress signal obtained from sample of material 4. The superimposed strain signal and the superimposed stress signal may individually be displayed on oscilloscope 86, e.g. along a vertical axis which is proportional to voltage against time along the horizontal axis, as above described. An illustrative oscilloscope display of isolated superimposed stress is shown in FIG. 8 of the drawings.

Figure 9:
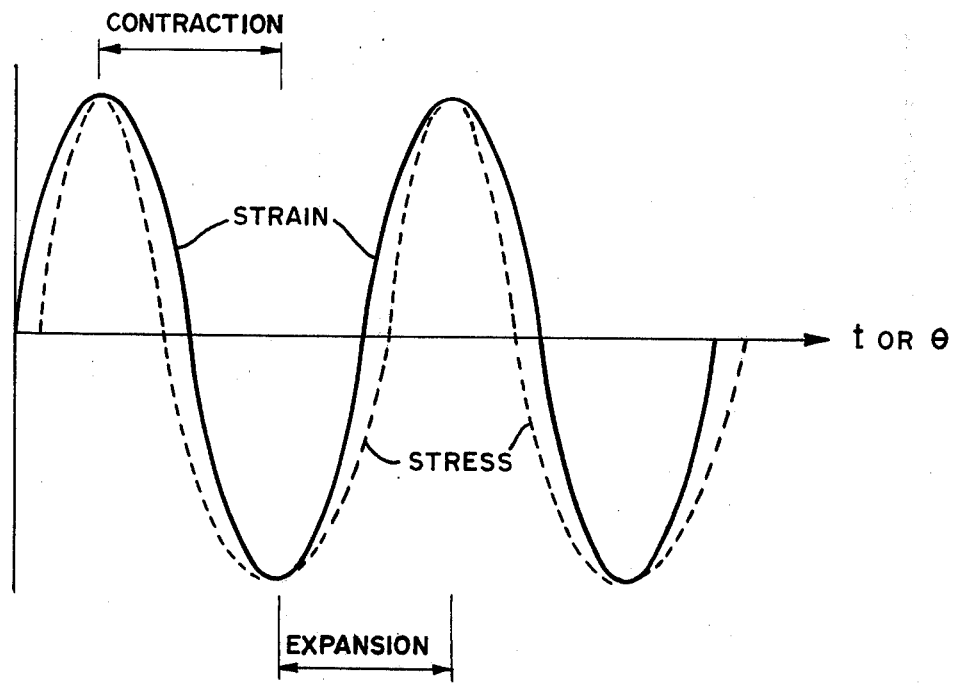
FIG. 9 is an illustration of a display of stress-strain variation, plotted with reference to time and angle.

For display purposes, the voltage peaks of the superimposed strain signal and of the isolated superimposed stress signal may be scaled to the same value, so that the peaks of the superimposed stress and the superimposed strain signals coincide in amplitude, a process sometimes referred to as "normalizing". Observation of the normalized, superimposed stress and superimposed strain signals, superimposed upon each other for display, as shown in FIG. 9, permits determination that there is a phase lag between the superimposed stress signal and the superimposed strain signal; whether the phase lag varies in amount as a function of time, and whether it varies in direction as a function of time. From the signals thus superimposed upon each other it can further be determined whether the phase lag between the superimposed stress signal and the superimposed strain signal additionally varies as a function of the cyclic strain applied by the first displacement generator, which would be indicated by cyclic changes in the phase lag in phase with the cyclic strain applied by the first displacement generator. From the superimposed signals one may further determine whether there is a change in amplitude of the superimposed stress signal resulting from the cyclic strain applied by the first displacement generator, which change in amplitude is a function of the strain applied by the first displacement generator. The change in amplitude of the superimposed stress signal as a function of the strain applied by the first displacement generator can be measured directly on the display.

Figure 10:
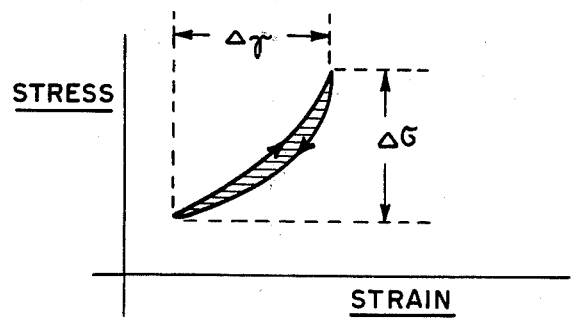
FIG. 10 is an illustration of a display of stress plotted against strain.

Still referring to FIG. 6, the superimposed strain signal obtained from signal conditioner 96 and the isolated superimposed stress signal represented by the output of adder 82 in differential testing, as above described, may also be displayed against one another on the oscilloscope 86, instead of being displayed in reference to time. When a voltage proportional to the superimposed stress signal is displayed along the vertical axis, and a voltage proportional to the ioslated superimposed strain signal derived from differential testing is displayed along the horizontal axis, the resulting display shows a hysteresis loop, as illustrated by FIG. 10. The area within the hysteresis loop represents the energy dissipated by the sample of material 4 during one cycle of testing involving the displacement by the second displacement generator 12 only, which is superimposed upon that of first displacement generator 10. The area enclosed by the hysteresis loop represents the difference between the energy applied to the sample of material 4 during expansion of the sample, and the energy released by the sample during contraction. The area can be determined by photographing the hysteresis loop displayed on the oscilloscope 86. The area enclosed by the loop on the photograph can be determined by conventional techniques, such as by polynominal regression, by use of a planimeter, or by weighing the cut-out loops.

Figure 8:
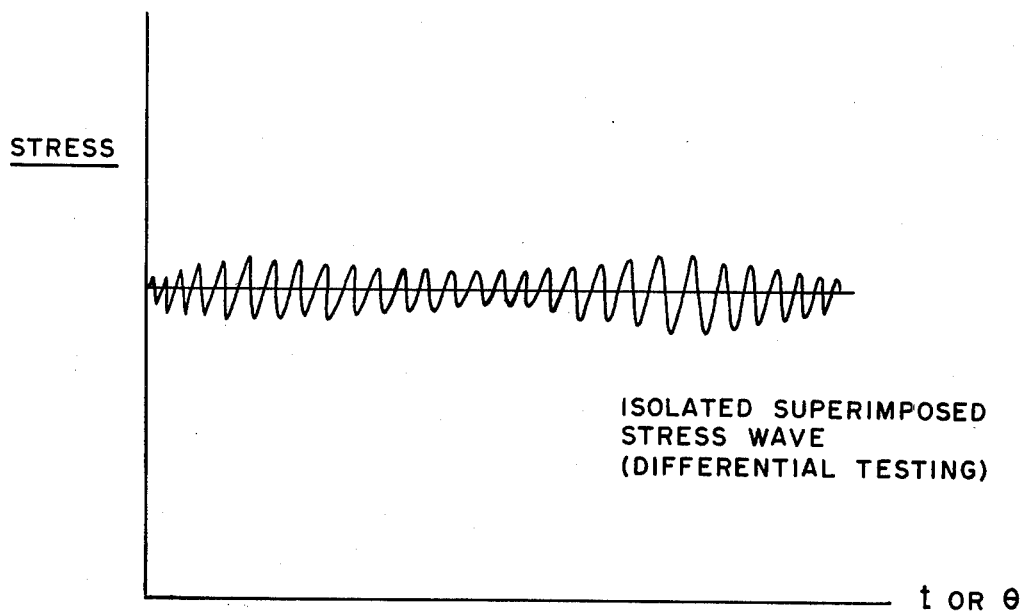
FIG. 8 is an illustration of a display of a strain signal obtained by differential testing.

If there is a cyclic change in amplitude of the superimposed cyclic stress wave, in phase with the basic strain applied to the material being tested by differential testing, then the isolated superimposed stress signal, if displayed on an oscilloscope as a series of waves, will show an undulating wave as illustrated in FIG. 8. If a single wave of the isolated superimposed stress signal is displayed on the oscilloscope, that single wave will undergo cyclic changes in amplitude in phase with the basic strain applied to it. Similarly, if there is a phase lag between the superimposed stress signal and the isolated superimposed strain signal, and that phase lag varies in amount and/or direction as a function of the basic strain, and the isolated superimposed strain signal is displayed on an oscilloscope, then the wave form will change in phase with the basic strain applied by first displacement generator 10. If the isolated superimposed stress signal and the superimposed strain signal are displayed against each other on an oscilloscope to show a hysteresis loop, the area enclosed by the loop will vary in phase with the basic strain applied by first displacement generator 10. To aid in determination of changes in amplitude and phase lag of the superimposed stress signal as a function of the basic strain applied to the material subjected to strain generated by both the first and the second displacement generators, it is desirable to isolate for display purposes individual waves, or short segments of consecutive waves, of the isolated superimposed stress signal at various angles ($\theta$) of displacement of the first displacement generator. This may, for example, be conveniently accomplished by use of mechanical electrical breaker means associated with drive shaft 63 of first displacement generator 10.

Figure 11:
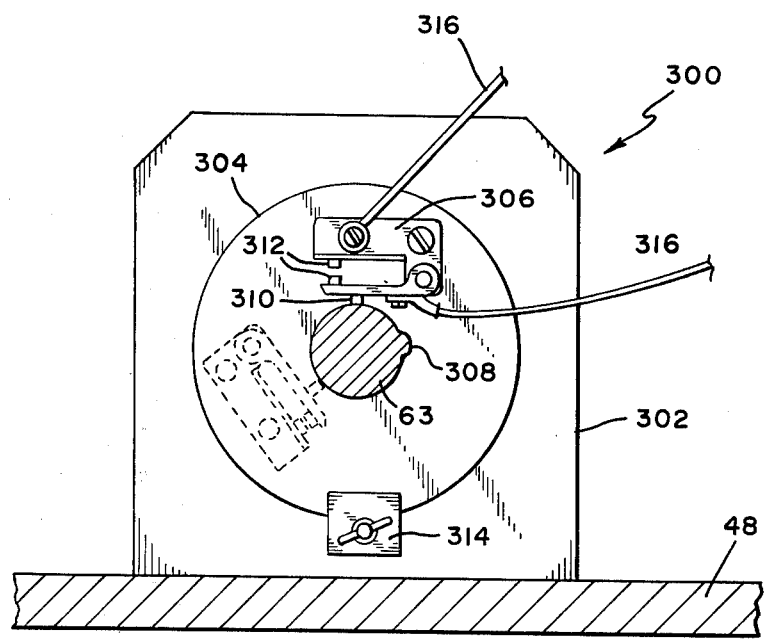
FIG. 11 is a frontal view of optional mechanical-electrical breaker means for isolating individual waves, or short segments of consecutive waves of the isolated superimposed stress signal in differential testing.

With reference to FIG. 11, mechanical-electrical breaker means 300 for isolating individual waves, or short segments of consecutive waves, of the isolated superimposed stress signal at any given angle ($\theta$) of displacement of the first displacement generator are mounted on platform 48 and are associated with drive shaft 63 of first displacement generator 10. Breaker means 300 comprise mounting bracket 302, contact point plate 304, and contact point assembly 306. Mounting bracket 302 and contact point plate 304 surround drive shaft 63. Mounting bracket 302 has an aperture through which drive shaft 63 extends. Contact point plate 304 is rotably mounted within the aperture of mounting bracket 302. Contact point plate 304 also has an aperture through which drive shaft 63 extends, concentric with the aperture of mounting bracket 302. Contact point assembly 306 is mounted on contact point plate 304. Contact point assembly 306 is provided with a cam follower 310 and contact points 312, which are held in normally open position. Cam follower 310 is in sliding engagement with drive shaft 63. Drive shaft 63 is provided with cam 308. Rotation of drive shaft 63 brings cam 308 in contact with cam follower 310, thereby closing the contact between contact point 312 for short periods at predetermined angular positions of drive shaft 63, hence at predetermined angular displacement provided by first displacement generator 10. Contact points 312 are held in closed position for period of time corresponding to at least one full phase of displacement imposed on the sample of material 4 by second displacement generator 12, but may be held in closed position for longer period of time to cover a shot segment of superimposed strain waves, say in the order of 2 to 5, or more waves. Duration of contact closure is determined by the shape of cam 308. The output from adder 82, which represents the superimposed stress signal obtainer from sample of material 4, is conducted to contact points 312 by means of leads 316, where it is broken into segments corresponding to a particular angular displacement by the first displacement generator 10.

Contact point plate 304 is rotably mounted within the aperture formed within mounting bracket 302 to permit rotation of contact point plate 304 around drive shaft 63, to thereby selectively extract signals corresponding to individual waves, or short segments of waves, of superimposed stress at any desired angle ($\theta$) of displacement imposed by first displacement generator 10. By means of clamping means 314 mounted on mounting bracket 302, contact point plate 304 may be locked in any particular chosen angular position. The contact point assembly shown in dotted lines in FIG. 11 illustrates a second position for the contact point assembly achieved by rotating contact point plate 304. By displaying the resultant segment of the superimposed stress signal obtained by means of mechanical-electrical breaker means 300, e.g. on oscilloscope 86 in the manner above described, one can determine amplitude, phase lag and hysteresis loop (including the area enclosed within the hysteresis loop) for the stress generated within sample of material 4 by the superimposed strain applied by second displacement generator 12, at any particular angle of displacement ($\theta$) applied by first displacement generator 10, so that it is possible to obtain the material modulus and the mechanical lows for each instant of the experiment.

The area of the hysteresis loop may also be electronically integrated by integrating means 28 (FIG. 6). To that end, the differentiated superimposed strain signal from optional fifth force transforming means 226 is processed in a signal conditioner 96, which includes an amplifier and a power supply. The power supply supplies power to the electronic cell 81 of the fifth force transforming means 226. As an output from a signal conditioner 96, the differentiated strain signal is conducted to amplifier 99 of the integrator means 28. The isolated superimposed stress signal from amplifier 97 and the differentiated strain signal from amplifier 99 are conducted to multiplier 100 of integrator means 28. The output from the multiplier 100 is conducted through an integrating amplifier 102, and then to a voltmeter 104, such as a digital voltmeter. The isolated superimposed stress signal and/or the superimposed differentiated strain signal are also conducted to a peak finder 106, which measures the peak-to-peak voltage of the isolated superimposed stress signal. A sequencing cam switch means is provided which operates in conjunction with rotable shaft 204 of second displacement generator 12. The sequencing cam switch means controls and freezes for "display" the accumulation of voltage in capacitor 105 (FIG. 6) corresponding to the area of the hysteresis loop. After a predetermined number of cycles of rotation of shaft 204, the cam switch means activates a zero switch means 103 (FIG. 6) to reset the digital voltmeter 104 (FIG. 6). Means, such as a peak finder 106 and a digital voltmeter 104 are provided to measure the voltages which are proportional to the ratio of the change in the stress signal ($\sigma$) to the change in the strain signal ($\gamma$). This ratio is called a complex modulus (E*):

$$E^* = (\Delta \sigma / \Delta \gamma)$$

When the phase lag is angle dependent, the storage modulus (E') is defined as: $E' = E \cos \delta(\theta)$, wherein $\delta$ is the phase lag, and the loss modulus (E'') is defined as $E'' = E \sin \delta (\theta)$ With switch 89 (FIG. 6) in the upper position, opposite to the position illustrated in FIG. 6, the basic stress and strain signals, and the differentiated basic strain signals for sample 4a may be processed, displayed, and analyzed in manner analogous to that above described.

Further, the composite stress signal obtained from first force transforming means 14 as an output from a signal conditioner 96 is also conducted to a pretension control 108, such as the servo motor 44 of the pretension means 8 (FIG. 1) to provide a constant tension on the sample of material 4, and, optionally, 4a being tested.

Temperature Chamber

Figure 12:
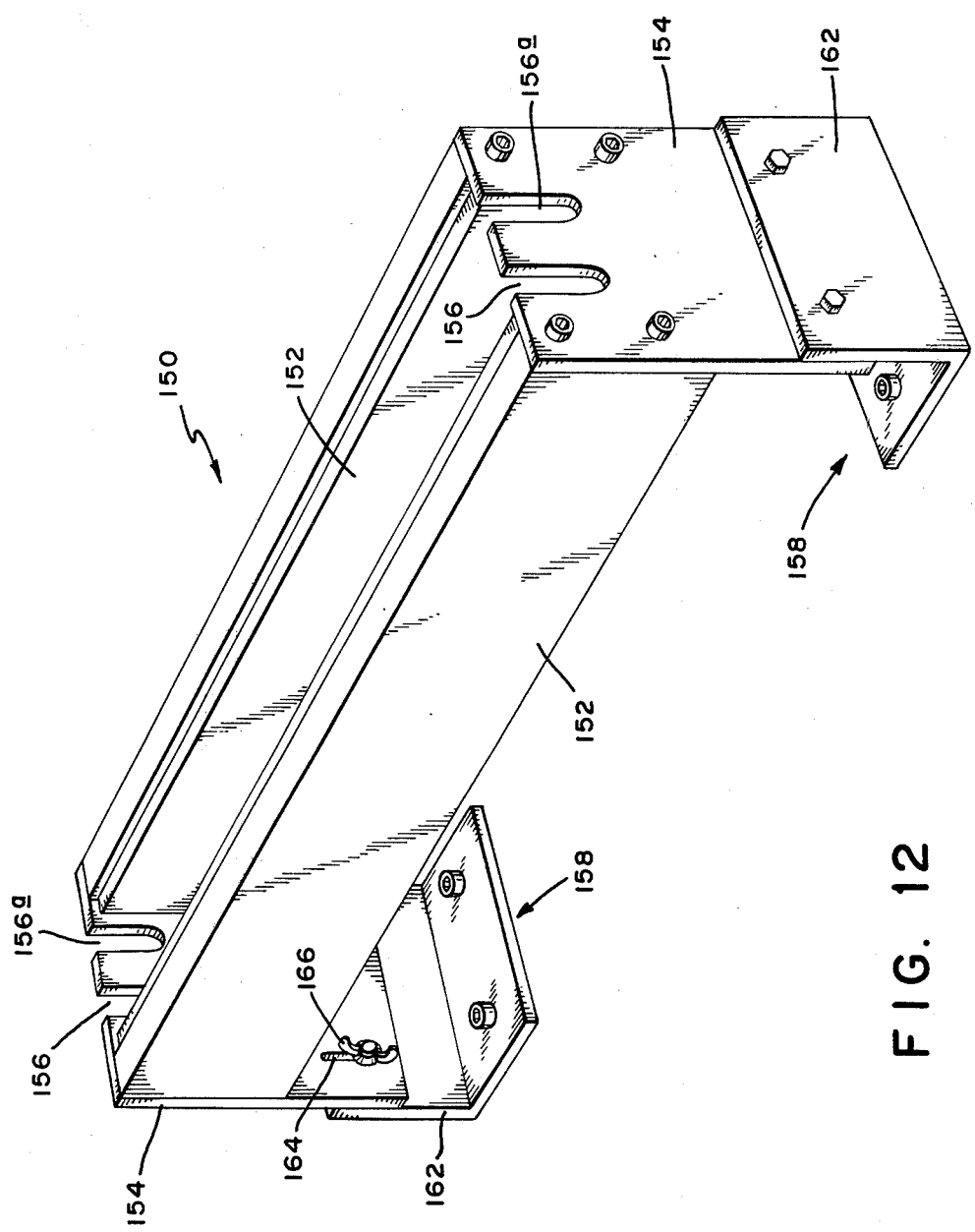
FIG. 12 is an isometric view of a temperature chamber.

If it is desired to test the material 4 in the presence of heat, a temperature chamber is preferably provided. Referring to FIG. 12, the temperature chamber (referred to generally by the numeral 150) is an enclosed elongated structure having two sides 152, a bottom (not shown), and two opposed ends 154. Each of the ends 154 has a slot 156, and, optionally, 156(a) therein. A portion of the active wire 30, and, optionally 30(a) extends through one of the slots 156 (and 156(a), respectively) into the temperature chamber 150. A portion of the passive wire 32, and, optionally 32(a) extends through the other slot 156 (and 156(a), respectively) at the opposite end into the temperature chamber 150. The temperature chamber 150 also includes a cover, not shown, adapted to fit on top of the temperature chamber 150. The viscoelastic material 4 (and, optionally, 4a) to be tested is placed into the temperature chamber 150 and the top is placed on the temperature chamber 150 thereafter. The material is held in the temperature chamber 150 by the material end of the active wire(s) and the material end of the passive wire(s). The temperature chamber 150 also includes at least one thermocouple. The thermocouple senses temperature. Preferably, heat is supplied to the temperature chamber 150 by means of electrical resistors embedded in the interior of the sides 152 of the temperature chamber 150. An automatic temperature control means is provided to maintain the temperature in the temperature chamber 150 at a desired level. Thus, the temperature chamber 150 is an enclosure in which the material can be conveniently inserted and removed and which is adapted to provide an environment in which the temperature may be conveniently controlled and varied as desired.

A support structure, referred to generally by the numeral 158, is provided at each end of the temperature chamber 150 for mounting the temperature chamber 150 on a platform, such as the platform 48 shown in FIG. 1. The support structure 158 includes an L-shaped bracket 162 at each end of the temperature chamber 150. Each L-shaped bracket 162 may be made in two parts, having slots 164 and wing nuts 166 to allow adjustment of the height of the temperature chamber 150.

Position Transforming Means

Referring to FIGS. 1 and 2, position transforming means 20 may be a linear variable differential transformer. The position transforming means 20 is connected to the movable member 40 of the pretension means 8. The function of the position transforming means 20 is to transform instantaneous changes in elongation of the material 4 into an electronic elongation signal.

The holding means of the apparatus of the present invention may be modified, for example in the manner shown in U.S. Pat. No. 3,969,930, to provide for tension testing of materials other than, say, fiber or cord, such as strips, etc., and for testing under shear and compression.

We claim:

1. An apparatus for testing a viscoelastic material, comprising:
   a. holding means connected to the material for holding the material in a predetermined position during testing;
   b. pretension means coupled to the material for applying tension to the material during testing;

c. a first displacement generator having an eccentric means coupled to the material for applying cyclic displacement to the material;

d. a second displacement generator having an eccentric means coupled to the material for applying cyclic displacement to the material co-directional with the cyclic displacement applied by the first displacement generator; and e. mechanical-electrical transforming means coupled to the material for transforming mechanical motions into electrical signals.

2. The apparatus for testing viscoelastic material according to claim 1 wherein the cyclic displacement applied to the material by the second displacement generator is of smaller amplitude and higher frequency that the displacement applied to the material by the first displacement generator.

3. The apparatus for testing viscoelastic material according to claim 1 wherein the mechanical-electrical transforming means comprises first force transforming means for transforming mechanical stress developed in the material into an electrical stress signal.

4. The apparatus for testing viscoelastic material according to claim 1 further comprising a temperature chamber for controlling the temperature of the environment in which the material is held during testing.

5. Apparatus for testing viscoelastic material according to claim 1 wherein the cyclic displacement applied to the material by the second displacement generator is of amplitude such that the ratio of the amplitude of the cyclic displacement applied by the second displacement generator to the amplitude of the displacement by the first displacement generator is within the range of from about 1:5 to about 1:100, and the frequency of the cyclic displacement applied by the second displacement generator is from about 20 to about 200 times the frequency of the cyclic displacement applied by the first displacement generator.

6. Apparatus for testing viscoelastic material according to claim 5 wherein the mechanical-electrical transforming means comprises a first force transforming means for transforming mechanical stress developed in the material into an electrical stress signal, and further comprising display means for said electrical stress signal.

7. Apparatus for testing a viscoelastic material according to claim 6 further comprising a temperature chamber for controlling the temperature of the environment in which the material is held during testing.

8. Apparatus for testing a viscoelastic material according to claim 6 wherein the display means for said electrical stress signal comprises an oscilloscope.

9. Apparatus for testing a viscoelastic material to determine physical-structural properties of the material, adapted to differential testing of duplicate samples of the material, comprising:

a. holding means connected to the material for holding the material in a predetermined position during testing;

b. pretension means coupled to the material for applying tension to the material during testing;

c. a first displacement generator having an eccentric means coupled to the first and the second sample of the material for applying cyclic displacement to the material;

d. a second displacement generator having an eccentric means coupled to the first sample of the material for applying cyclic displacement to the first sample of the material co-directional with the cyclic displacement applied by the first displacement generator; and e. mechanical-electrical transforming means coupled to the first sample of material, and mechanical-electrical transforming means coupled to the second sample of material, for transforming mechanical motions into electrical signals.

10. Apparatus for testing viscoelastic material according to claim 9 wherein the mechanical-electrical transforming means comprise:

a. force transforming means for transforming mechanical stress developed in the first sample of the material by action of the first and second displacement generators into a composite electrical stress signal; and b. force transforming means for transforming mechanical stress developed in the second sample of the material by action of the first displacement generator into an electrical stress signal.

11. Apparatus for testing viscoelastic material according to claim 10 further comprising means for generating an electrical stress signal representing the difference between the electrical stress signals obtained from the first and the second samples of the material.

12. Apparatus for testing a viscoelastic material according to claim 11 further comprising display means for the electrical stress signal representing the difference between the electrical stress signals obtained from the first and the second samples of the material.

13. Apparatus for testing a viscoelastic material according to claim 12 wherein the display means comprise an oscilloscope.

14. Apparatus for testing a viscoelastic material according to claim 11 wherein the mechanical-electrical transforming means further comprise force transforming means for transforming strain applied to the first sample of the material by the second displacement generator into an electrical strain signal.

15. Apparatus for testing a viscoelastic material according to claim 14 further comprising a differentiating means for generating a differentiated strain signal of the strain applied to the first sample of the material by the second displacement generator.

16. Apparatus for testing a viscoelastic material according to claim 14 further comprising means for successively isolating discrete individual waves, or short segments of consecutive waves, of the electrical stress signal representing the difference between the electrical stress signals obtained from the first and the second samples of the material, at any desired angle of displacement applied by the first displacement generator.

17. Apparatus for testing a viscoelastic material according to claim 16 further comprising differentiating means for generating a differentiated strain signal of the strain applied to the first sample of the material by the second displacement generator.

18. Apparatus for testing of viscoelastic material according to claim 17 further comprising an integrating means for integration of a stress-strain hysteresis loop, and display means for displaying an output of the integrating means to measure the area of the hysteresis loop and thereby determine energy loss.

19. A method for testing viscoelastic material and measuring selected properties, comprising:

a. applying a basic first cyclic sinusoidal strain component to the material to be tested, having predetermined amplitude and frequency;

b. simultaneously applying a superimposed second sinusoidal strain component to the material to be tested, having predetermined amplitude and frequency; and c. transforming the stress resulting in the material from the strain applied by the first and second cyclic strain component into a composite electrical stress signal.

20. The method of claim 19 further comprising transforming the strain applied by the first cyclic strain component into an electrical strain signal having a cyclic strain wave form and an amplitude, and observing that there is a change in amplitude of that component of the composite stress signal resulting from the strain applied by the first cyclic strain component, which varies with the strain applied by the first cyclic strain component.

21. The method of claim 19 wherein the ratio of the amplitude of the first and second strain components is within the range of from about 1:5 to about 1:100, and wherein the frequency of the second strain component is from about 20 to 200 times the frequency of the first strain component.

22. The method of claim 19 adapted to differential testing of duplicate samples of material comprising:

a. applying a basic first cyclic sinusoidal strain component to a first sample of the material to be tested, having predetermined amplitude and frequency; simultaneously applying a superimposed second sinusoidal strain component to the first sample of the material to be tested, having predetermined amplitude and frequency; and transforming the stress resulting in the first sample of the material from the strain applied by the first and second cyclic strain components into a composite electrical stress signal;

b. simultaneously applying the basic first cyclic sinusoidal strain component to a second sample of the material to be tested, and transforming the stress resulting in the second sample of the material from the strain applied by the first cyclic strain component into an electrical stress signal; and c. generating a differential electrical stress signal representing the stress generated in the first sample of the material from application of the superimposed second sinusoidal strain component as the difference between the stress signals obtained from the first and second samples of the material.

23. The method of claim 22 further comprising:

a. transforming the strain applied by the second cyclic strain component into an electrical strain signal having a cyclic strain wave form and an amplitude;

b. displaying the differential electrical stress signal and the electrical strain signal obtained in step (a), above, as a function of time on the same scale and arranging the amplitude of the stress wave form and the strain wave form to be equal;

c. observing that there is a change in amplitude in the isolated electrical stress signal in phase with the strain applied by the first cyclic strain component, and/or that there is a phase lag between the strain wave form applied by the superimposed second strain component and the isolated stress wave form resulting therefrom, and that the phase lag varies in amount and sometimes in direction, in phase with the strain applied by the first cyclic strain component.

24. The method of claim 23 wherein the ratio of the amplitude of the first and second strain components is within the range of from about 1:5 to about 1:100, and wherein the frequency of the second strain component is from about 20 to 200 times the frequency of the first strain component.

25. The method of claim 22 further comprising isolating successive waves or short segments of waves of the differential stress signal at predetermined angles of the basic first cyclic sinusoidal strain component, and displaying the isolated successive waves, or short segments of waves, of the differential stress signal along a vertical axis; displaying the corresponding strain wave along a horizontal axis; and observing the formation of a hysteresis loop.

26. The method of claim 25 further comprising obtaining separate hysteresis loops for different angles of the first basic cyclic sinusoidal strain component, measuring the areas within the separate hysteresis loops, and observing that the areas enclosed within the separate hysteresis loops vary as a function of the angle of the basic first cyclic sinuosidal strain component.

27. The method of claim 22 further comprising isolating successive waves, or short segments of waves, of the differential stress signal at predetermined angles of the basic first cyclic sinusoidal strain component; transforming the superimposed second sinusoidal strain component into a differentiated strain signal; and integrating said isolated differential stress signal and said differentiated strain signal to determine the area of the hysteresis loop.

28. The method of claim 27 wherein the step of transforming the superimposed second sinusoidal strain component into a differentiated strain signal comprises differentiating said strain signal mechanically.

29. The method of claim 28 wherein the ratio of the amplitude of the first and second strain components is within the range of from about 1:5 to about 1:100, and wherein the frequency of the second strain component is from about 20 to 200 times the frequency of the first strain component.

30. The method of claim 29 further comprising integrating isolated differential stress signals and said differential strain signal for different angles of the first basic cyclic sinusoidal strain component, and observing that the areas of the corresponding hysteresis loops vary as a function of the angle of the basic first cyclic sinusoidal strain component.

* * * * *

UNITED STATES PATENT AND TRADEMARK OFFICE
CERTIFICATE OF CORRECTION

PATENT NO. : 4,056,973
DATED : November 8, 1977
INVENTOR(S) : Dusan C. Prevorsek, Young D. Kwon & Raj K. Sharman It is certified that error appears in the above-identified patent and that said Letters Patent are hereby corrected as shown below:

Column 1, line 13, "sinuosoidal" should read -- sinusoidal --.

Column 6, line 21, after "4" insert -- inches --.

Column 6, line 26, after "2" insert -- inches --.

Column 8, line 6, "physical-structural" should read -- physical - structural --.

Column 8, line 59, "90 °" should read -- 90° --.

Column 17, line 15, " that" should read -- than --.

Column 17, line 32, after "displacement" insert -- applied --.

Signed and Sealed this

Fourth Day of July 1978

[SEAL]

Attest:

RUTH C. MASON
*Attesting Officer*

DONALD W. BANNER
*Commissioner of Patents and Trademarks*